(12) United States Patent
Solomon et al.

(10) Patent No.: US 11,324,939 B2
(45) Date of Patent: May 10, 2022

(54) METHODS AND DEVICES FOR VASCULAR ACCESS

(71) Applicant: I-V Access Technology, Inc., San Francisco, CA (US)

(72) Inventors: Clint Solomon, Morgan Hill, CA (US); Vincent Leskowich, Oakhurst, NJ (US); Thomas Sutton, Summit, NJ (US); James Hale, Los Osos, CA (US); Jacob Hentzler, Morgan Hill, CA (US)

(73) Assignee: I-V Access Technology, Inc., San Francisco, CA (US)

( * ) Notice: Subject to any disclaimer, the term of this patent is extended or adjusted under 35 U.S.C. 154(b) by 0 days.

(21) Appl. No.: 17/307,766

(22) Filed: May 4, 2021

(65) Prior Publication Data

US 2021/0268238 A1 Sep. 2, 2021

Related U.S. Application Data

(63) Continuation-in-part of application No. 17/074,231, filed on Oct. 19, 2020, which is a continuation of
(Continued)

(51) Int. Cl.
| | |
|---|---|
| *A61M 39/26* | (2006.01) |
| *A61M 25/06* | (2006.01) |
| *A61M 39/10* | (2006.01) |
| *A61M 39/04* | (2006.01) |
| *A61M 39/00* | (2006.01) |

(Continued)

(52) U.S. Cl.
CPC ........ *A61M 39/26* (2013.01); *A61M 25/0606* (2013.01); *A61M 25/0625* (2013.01); *A61M 39/045* (2013.01); *A61M 39/1011* (2013.01); *A61M 25/0097* (2013.01); *A61M 25/0631* (2013.01); *A61M 29/00* (2013.01); *A61M 39/06* (2013.01); *A61M 2025/0687* (2013.01); *A61M 2039/0036* (2013.01)

(58) Field of Classification Search
CPC .......... A61M 25/0606; A61M 25/0625; A61M 39/1011; A61M 25/0097; A61M 25/0631; A61M 29/00; A61M 39/26; A61M 2025/0687; A61M 2039/064; A61M 2039/2426; A61M 2039/0036; A61M 39/02; A61M 39/045; A61M 39/06
See application file for complete search history.

(56) References Cited

U.S. PATENT DOCUMENTS

| | | | |
|---|---|---|---|
| 3,195,786 | A | 7/1965 | Vogt |
| 3,347,232 | A | 10/1967 | Abraham |

(Continued)

FOREIGN PATENT DOCUMENTS

| | | |
|---|---|---|
| CN | 203694357 | 7/2014 |
| EP | 0653220 | 5/1995 |

(Continued)

*Primary Examiner* — Theodore J Stigell
(74) *Attorney, Agent, or Firm* — Levine Bagade Han LLP

(57) ABSTRACT

Valve assemblies having improved ability to selectively control flow of fluids through the catheter and prevent leakage of fluids from the proximal end of a catheter that is positioned within a patient. Such improved catheter valve assemblies also prevent leakage of fluids after repeated insertion and removal of medical instruments through the valve.

26 Claims, 13 Drawing Sheets

Related U.S. Application Data application No. 16/670,291, filed on Oct. 31, 2019, now Pat. No. 10,850,069, which is a continuation of application No. 16/520,813, filed on Jul. 24, 2019, which is a continuation of application No. 16/004,970, filed on Jun. 11, 2018, now Pat. No. 10,406,326.

(60) Provisional application No. 63/151,562, filed on Feb. 19, 2021, provisional application No. 62/552,663, filed on Aug. 31, 2017.

(51) Int. Cl.
A61M 25/00 (2006.01)
A61M 29/00 (2006.01)
A61M 39/06 (2006.01)

(56) References Cited

U.S. PATENT DOCUMENTS

| | | |
|---|---|---|
| 3,861,416 A | 1/1975 | Wichterle |
| 4,341,239 A * | 7/1982 | Atkinson ............ F16K 15/147 137/493 |
| 4,465,102 A | 8/1984 | Rupp |
| 4,524,805 A | 6/1985 | Hoffman |
| 4,565,545 A | 1/1986 | Suzuki |
| 4,588,398 A | 5/1986 | Daugherty et al. |
| 4,629,450 A | 12/1986 | Suzuki et al. |
| 4,655,752 A | 5/1987 | Honkanen et al. |
| 4,758,225 A | 7/1988 | Cox et al. |
| 4,950,257 A | 8/1990 | Hibbs et al. |
| 5,010,925 A | 4/1991 | Atkinson et al. |
| 5,092,857 A | 3/1992 | Fleischhacker |
| 5,114,408 A * | 5/1992 | Fleischhaker ..... A61M 39/0606 604/167.04 |
| 5,122,118 A | 6/1992 | Haber et al. |
| 5,129,884 A | 7/1992 | Dysarz |
| 5,176,650 A | 1/1993 | Haining |
| 5,242,410 A | 9/1993 | Melker |
| 5,295,658 A | 3/1994 | Atkinson et al. |
| 5,405,323 A | 4/1995 | Rogers et al. |
| 5,445,617 A | 8/1995 | Yoon |
| 5,456,284 A | 10/1995 | Ryan et al. |
| 5,527,290 A | 6/1996 | Zadini et al. |
| 5,618,272 A | 4/1997 | Nomura |
| 5,713,876 A | 2/1998 | Bogert et al. |
| 5,843,046 A | 12/1998 | Motisi et al. |
| 6,035,896 A | 3/2000 | Liardet |
| 6,165,168 A | 12/2000 | Russo |
| 6,267,748 B1 | 7/2001 | Gulliksen et al. |
| 6,607,511 B2 | 8/2003 | Halseth et al. |
| 6,702,255 B2 | 3/2004 | Dehdashtian |
| 6,706,017 B1 | 3/2004 | Dulguerov |
| 6,716,197 B2 | 4/2004 | Svendsen |
| 6,817,989 B2 | 11/2004 | Svendsen et al. |
| 7,470,254 B2 | 12/2008 | Basta et al. |
| 7,736,339 B2 | 6/2010 | Woehr et al. |
| 7,753,338 B2 | 7/2010 | Desecki |
| 7,892,209 B2 | 2/2011 | Harand et al. |
| 7,938,805 B2 | 5/2011 | Harding et al. |
| 8,006,953 B2 | 8/2011 | Bennett |
| 8,092,432 B2 * | 1/2012 | Nordgren ............ A61M 39/24 604/247 |
| 8,105,288 B2 | 1/2012 | Keyser et al. |
| 8,469,928 B2 | 6/2013 | Stout et al. |
| 8,591,469 B2 | 11/2013 | Keyser et al. |
| 9,028,425 B2 | 5/2015 | Burkholz |
| 9,114,231 B2 | 8/2015 | Woehr et al. |
| 9,155,863 B2 | 10/2015 | Isaacson et al. |
| 9,155,864 B2 | 10/2015 | Stout et al. |
| 9,604,035 B2 | 3/2017 | Keyser et al. |
| 9,775,973 B2 | 10/2017 | Keyser et al. |
| 10,406,326 B2 | 9/2019 | Solomon |
| 10,850,069 B2 * | 12/2020 | Solomon ........... A61M 25/0625 |
| 2004/0092879 A1 | 5/2004 | Kraus et al. |
| 2004/0097880 A1 | 5/2004 | Schur |
| 2004/0193109 A1 | 9/2004 | Prestidge et al. |
| 2004/0236287 A1 | 11/2004 | Swenson et al. |
| 2005/0131350 A1 | 6/2005 | Shaw et al. |
| 2005/0187524 A1 | 8/2005 | Willis et al. |
| 2005/0256460 A1 | 11/2005 | Rome et al. |
| 2006/0200083 A1 | 9/2006 | Freyman et al. |
| 2007/0250037 A1 | 10/2007 | Brimhall et al. |
| 2007/0282268 A1 | 12/2007 | Mayse |
| 2008/0092571 A1 | 4/2008 | Allison et al. |
| 2008/0093571 A1 | 4/2008 | Desecki |
| 2008/0172003 A1 | 7/2008 | Plishka et al. |
| 2009/0209912 A1 | 8/2009 | Keyser et al. |
| 2009/0209914 A1 | 8/2009 | Koch et al. |
| 2011/0056569 A1 | 3/2011 | Chambo et al. |
| 2012/0150118 A1 | 6/2012 | Keyser et al. |
| 2012/0221024 A1 | 8/2012 | Sutton et al. |
| 2013/0204226 A1 | 8/2013 | Keyser |
| 2014/0058357 A1 | 2/2014 | Keyser et al. |
| 2014/0276432 A1 | 9/2014 | Bierman et al. |
| 2015/0265827 A1 | 9/2015 | Keyser et al. |
| 2016/0228654 A1 | 8/2016 | Rozwadowski et al. |
| 2016/0271370 A1 | 9/2016 | Keyser et al. |
| 2017/0326341 A1 | 11/2017 | Liska |
| 2018/0064912 A1 | 3/2018 | Keyser et al. |
| 2019/0060616 A1 | 2/2019 | Solomon |
| 2020/0016375 A1 | 1/2020 | Solomon |
| 2020/0061346 A1 | 2/2020 | Solomon |
| 2021/0031009 A1 | 2/2021 | Solomon |
| 2021/0290911 A1 | 9/2021 | Hentzler et al. |
| 2022/0001146 A1 | 1/2022 | Hentzler et al. |

FOREIGN PATENT DOCUMENTS

| | | |
|---|---|---|
| EP | 1291035 | 3/2003 |
| FR | 2655859 | 6/1991 |
| FR | 2687320 | 8/1993 |
| JP | 07-136285 | 5/1995 |
| JP | 09-047512 | 2/1997 |
| JP | 2007-260218 | 10/2007 |
| JP | 2011-234802 | 11/2011 |
| TW | 368422 | 9/1999 |
| TW | 592741 | 6/2004 |
| WO | WO 1992/016248 | 10/1992 |
| WO | WO 2003/013627 | 2/2003 |
| WO | WO 2009/091514 | 7/2009 |
| WO | WO 2013/119557 | 8/2013 |
| WO | WO 2019/046456 | 3/2019 |
| WO | WO 2021/194979 | 9/2021 |

* cited by examiner

METHODS AND DEVICES FOR VASCULAR ACCESS

CROSS-REFERENCE TO RELATED APPLICATIONS

This application is a continuation-in part of U.S. patent application Ser. No. 17/074,231, filed Oct. 19, 2020, which is a continuation of U.S. patent application Ser. No. 16/670,291, filed Oct. 31, 2019 (now U.S. Pat. No. 10,850,069), which is a continuation of U.S. patent application Ser. No. 16/520,813 filed Jul. 24, 2019, which is a continuation of U.S. patent application Ser. No. 16/004,970 filed Jun. 11, 2018 (now U.S. Pat. No. 10,406,326), which claims priority to U.S. Provisional Patent Application No. 62/552,663 filed Aug. 31, 2017. This application is also a non-provisional of U.S. Provisional Application No. 63/151,562 filed Feb. 19, 2021. The contents each of the above applications are incorporated herein by reference in their entirety.

FIELD OF THE INVENTION

The invention is directed to a valve assembly having improved ability to selectively control flow of fluids through the medical device and prevent leakage of fluids from the proximal end of the device that is positioned within a patient. Such improved valve assemblies also prevent leakage of fluids after repeated insertion and removal of medical instruments through the valve, such as catheters introducers, tubes, lines, ports that can be used for vascular or other devices. The valve assembly may also be used as a connection for needles (e.g., fistula needles), hemodialysis circuits, feeding tubes, urinary drain catheters, or any other suitable means.

BACKGROUND

Catheters allow medical practitioners to administer infusion or removal of fluids from a patient. For example, catheters can function as a conduit that allows infusion of fluids, such as normal saline solution, therapeutic substances, and/or nutritional fluids into a patient. Alternatively, catheters can withdraw fluids such as blood or other bodily fluids as required by the particular medical procedure. In those cases where the medical practitioner intends to position the catheter into a vessel, the medical practitioner will look for a flow of blood back into the catheter ("flashback") to verify placement of the catheter opening into a vessel. The number of different catheter insertion procedures and techniques is great and may include the use of a needle, dilator, stylet, or other medical device within the catheter when placed.

Once properly positioned, the catheter's hub (or medical device positioned within the catheter) can be coupled to an adapter (typically a luer fitting) to enable fluid coupling of the catheter to the source of fluids or reservoir. However, in the case of an accidental disconnection between the catheter and the reservoir, there is a possibility for the patient to bleed out or to entrain air that will lead to an embolism, both of which are potentially life-threatening for the patient. Accidental disconnection can occur if the mating parts are not securely tightened. The mating parts can also become loose from patient movement, unwanted fidgeting, or other patient interference. Further, if the patients have any blood-borne pathogen (e.g., HIV, hepatitis, etc.), blood exposure for the caregiver is potentially lethal. As such, insertion of the catheter requires that the point of access remains sanitary. The period between insertion of the catheter and coupling of an adaptor can cause bodily fluids to escape through the catheter, causing an unsanitary condition for the medical practitioner who must handle the catheter for coupling of the adapter and/or remove the medical device inserted through the catheter. The caregiver often covers an open connection port with their finger to reduce the blood flow until making a mating connection. Since blood can be a medium for bacterial growth, infection chances can rise due to exposure at the time of catheter insertion.

As such, there remains a need for a valve assembly that permits controlled fluid flow that also reduces risk of infection. There also remains a need for a valve that slows blood loss to give the caretaker time to adequately clean the connection and wipe away any residual blood on the connection. There also remains a need for a valve that minimizes the blood exposure for the caregiver at the time of insertion, removal, or a change in catheters. A valve assembly is described below.

SUMMARY

The illustrations and variations described herein are meant to provide examples of the methods and devices of the invention. It is contemplated that combinations of aspects of specific embodiments or combinations of the specific embodiments themselves are within the scope of this disclosure. The valve assemblies described herein can be used in any tubing assembly, especially medical tubing not only limited to catheter assemblies.

A valve assembly configured for use with a male luer having a distal end, a lateral surface, and a connector portion is provided. The assembly can be used as part of a catheter assembly where the valve assembly fits within a catheter hub. However, the valve assembly can be used in any assembly, especially those where valve deformation rather than fluid pressure opens the valve. Such assemblies include but are not limited to medical assemblies. For convenience, the examples below are discussed in relation to catheter assemblies. The catheter can comprise a catheter hub and a valve. The catheter hub can be configured to receive the male luer in a proximal end. The valve can be coupled to a chamber within the catheter hub and can comprise a barrier layer at a far end and a wall portion. The wall portion can extend proximally from the barrier layer towards a near end of the valve. The wall portion can define a valve cavity therein. The barrier layer can have at least one slit extending therethrough. An offset distance can be measured between a surface of the wall portion in the valve cavity and a surface of the chamber adjacent to barrier layer at the far end of the valve at the distal end. The offset distance can be less than a thickness of the barrier layer. The valve can be configured for positioning in the catheter hub such that the wall portion can engaged a surface of a chamber within the catheter hub. Insertion of the male luer into the valve cavity can cause the distal end of the male luer to open the at least one slit to permit fluid flow through the barrier layer. The lateral surface of the male luer can engage the wall portion at an interior of the valve cavity, causing the wall portion to engage the surface of the chamber.

The at least one slit can form a plurality of leaflets in the barrier layer. A perimeter of the at least one slit can be limited to the barrier layer such that the leaflets do not extend into the wall portion. The at least one slit can be branched such that the plurality of leaflets comprises at least three leaflets. A thickness of each of the plurality of leaflets can be the same. An entire outer surface of the wall portion can contact an inner surface of the catheter hub. The entire outer surface of the wall portion can comprise a cylindrical shape having a uniform outer diameter.

The valve assembly can further comprise a flange portion at a near portion of the valve. The flange can extend out of the chamber of the catheter hub to engage a proximal surface of an exterior of the catheter hub where the connector portion of the male luer can directly engage the flange portion against the proximal surface of the catheter hub. An outer diameter of the flange can be equal or less to an outer diameter of the proximal surface of the exterior of the catheter hub. The flange can be located within a recess in the chamber of the catheter hub. The flange can be located within a recess in a proximal surface of an exterior of the catheter hub. The valve can be axially recessed within the catheter hub. The wall portion can include at least one or more gaps to form at least one or more legs. The valve assembly can further comprise an insert positioned within the valve. The insert can be configured to receive the male luer. The valve assembly can further comprise a raised surface positioned within the valve. Wherein upon insertion of the male luer, the raised surface can be configured to be pushed by the male luer to open the valve.

The present disclosure is related to the following commonly assigned patents and applications, the entirety of each of which is incorporated by reference: U.S. Pat. Nos.: U.S. Pat. No. 8,105,288 issued on Jan. 31, 2012; U.S. Pat. No. 8,591,469 issued on Nov. 26, 2013; U.S. Pat. No. 9,775,973 issued on Oct. 3, 2017; U.S. Pat. No. 9,604,035 issued on Mar. 28, 2017; and U.S. Ser. No. 10/828,465 issued on Nov. 10, 2020. U.S. publication nos.: US20200016375A1 published on Jan. 16, 2020, and US20210031009A1 published on Feb. 4, 2021. Provisional application No. 62/993,493 filed on Mar. 23, 2020; 63/037,496 filed on Jun. 10, 2020; and 63/037,841 filed on Jun. 11, 2020.

BRIEF DESCRIPTION OF THE DRAWINGS

Each of the following figures diagrammatically illustrates aspects and variations to better understand the invention. Variation of the invention from the aspects shown in the figures is contemplated.

DETAILED DESCRIPTION

For a better understanding of the present invention, reference will be made to the following description of the embodiments, which is to be read in association with the accompanying drawings, which are incorporated in and constitute a part of this specification, show certain aspects of the subject matter disclosed herein and, together with the description, help explain some of the principles associated with the disclosed implementations.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising. (i.e., open language). The term "coupled", as used herein, is defined as connected, although not necessarily directly, and not necessarily mechanically.

Reference throughout this document to "some embodiments", "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

Figure 1A:
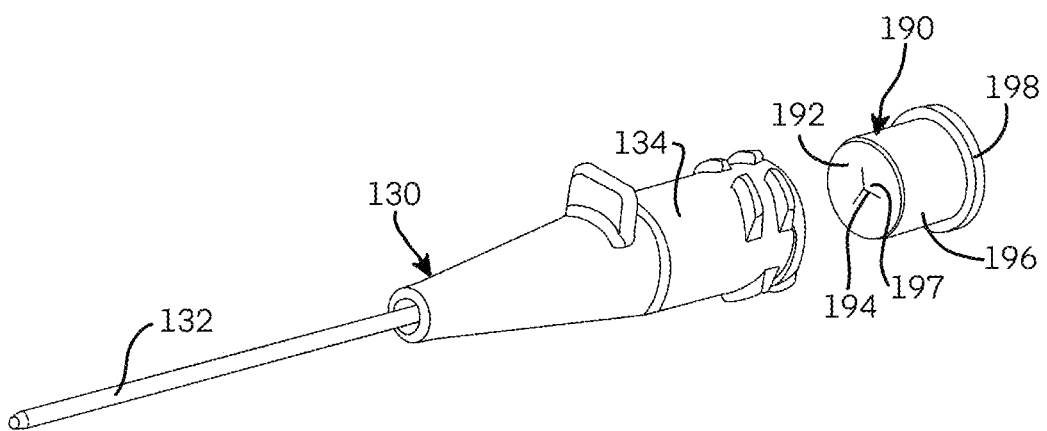
FIGS. 1A to 1K illustrate examples of an improved valve for use with catheters or other medical devices/introducers.
Figure 1B:
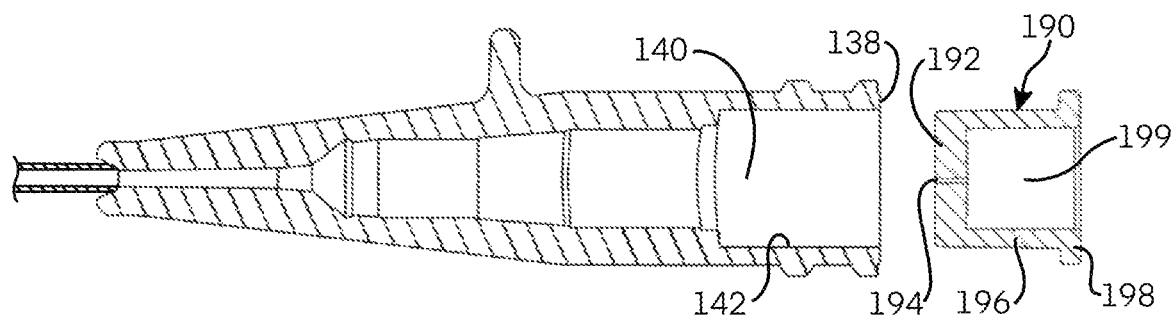
Figure 1C:
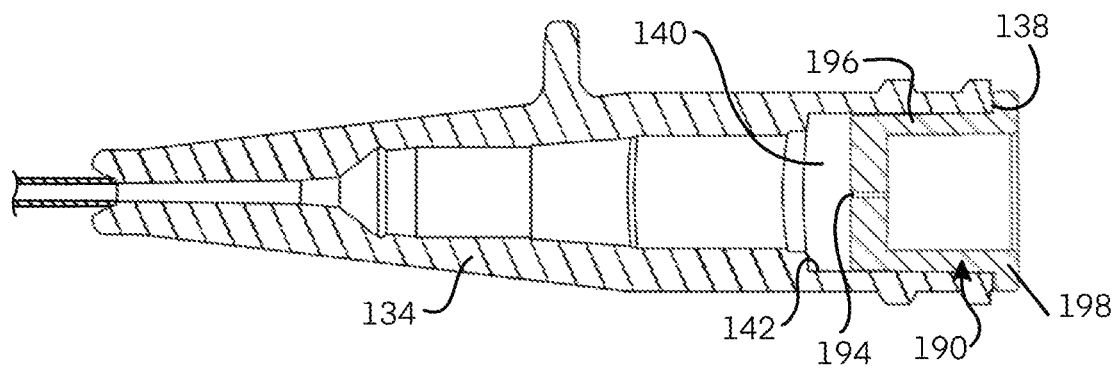

FIGS. 1A to 1C illustrate an improved valve for use with catheters or other medical devices/introducers. Typically, such a catheter 130 is used with a male luer (as described in FIGS. 5A-5G below). The catheter 130 includes a catheter hub 134, having a chamber 140 with a proximal surface 138 defining an open proximal end. The chamber 140 is in fluid communication with a catheter tubing 132 that is coupled to the catheter. The tubing includes one or more lumens in fluid communication with the chamber 140. The valve or septum valve 190 includes a barrier layer (or septum) 192 at a distal end. The barrier layer 192 can have one or more slits 194. The illustrated variation shows a barrier layer 192 with 3 slits 194 that form three leaflet structures 197 or flaps. However, variations of the valve 190 include any number of slits forming any number of leaflets. The barrier layer 192 generally includes a flexible or semi-flexible material that is compatible with exposure to blood, medicaments, and other fluids commonly encountered during catheterization/infusion procedure.

As shown in FIG. 1B, the valve includes a wall portion 196 extending proximally from the barrier layer 192 and defines a valve cavity 199. In the variation shown in FIGS. 1A to 1B, the valve 190 includes a flange portion 198 that is formed around the wall 196 at a proximal end of the valve 190. The flange portion 198 comprises a diameter greater than a diameter of the wall portion 196 for sealing against a proximal surface 138 of the catheter hub 134. Variations of the valve 190 include a flange portion 198 that encircles the valve 190. Alternatively, the flange portion 198 can include openings or segments such that it is not circumferentially continuous about the wall.

FIG. 1C shows the valve 190 coupled to the catheter hub 134 such that the flange portion 198 engages the proximal surface 138 of the catheter hub 134 and is exterior to the chamber 140 of the hub 134. The wall portion 196 of the valve 190 engages a surface of the chamber. The walls of the chamber 140 can be straight or can comprise any luer taper angle. Likewise, the walls of the valve can comprise a taper angle on the exterior and/or interior (e.g., the surface defining the cavity 199). The valve 190 can be affixed to the catheter at various points. For example, variations of the assembly include a valve 190 that is only affixed to the catheter hub 134 at the flange portion 198 using an adhesive or joining material where the wall portion 196 is simply positioned against a wall of the chamber 140. Alternatively, or in combination, the valve 190 can be affixed to the catheter hub 134 at the exterior wall portion 196. In an alternate variation, the valve 190 can simply be press-fit into the catheter hub 134. Any number of features known to those in the art can be used to facilitate seating of the valve 190 within the catheter hub 134 (e.g., pockets, ribs, increased frictional resistance of the surface of the valve or chamber, etc.)

The variations of valve 190 shown in FIGS. 1A to 1C also illustrate a valve 190 having a barrier layer 192 that is thicker than the wall portion 196. A thicker wall on the slit 194 face was found to increase the sealing surface. For example, the increased thickness of the wall 192 along the slit 194 permits the slit 194 to return to a closed position rather than remaining deformed by insertion of a medical device (see e.g., FIGS. 5B and 5C). The relatively thinner wall portion 196 shown in FIGS. 1A to 1C reduces an offset distance between the internal diameter of the valve cavity 199 and the internal wall 142 of the hub chamber 140. Reducing this offset allows for insertion of a male luer to a sufficient depth along a longitudinal axis to open the slit 194 at the barrier layer 192 of the valve without being impeded by the wall 196 of the valve 190. For example, a thickness of a wall 196 of a valve 190 must be selected such that the internal diameter of a valve cavity 199 is sufficiently large to allow insertion of a male luer into the cavity 199 when the valve is placed within the chamber 140 of the catheter hub. However, if a valve wall 196 is too thin, then the valve may suffer from an increased risk of failure (e.g., cracking or splitting) or a thin wall can present manufacturing difficulties in forming the valve. The variation of the valve 190 having sidewalls 196 that are thinner than the barrier layer 192 allows a slit 194 layer 192, having increased material thickness such that it is relatively more rigid, allowing the slit 194 to close fully and increases the likelihood that the slit returns to its original state to close the valve. Again, having a barrier layer 192 (i.e., the wall with the slit 194 formed therein) that is thicker than the sidewalls 196 increases the ability of the valve to close while the thinner sidewalls allow for insertion of a male luer into the cavity 199. In some variations, the thickness differential also allows deformation of the valve to occur at the septum rather than the wall portion.

Figure 1D:
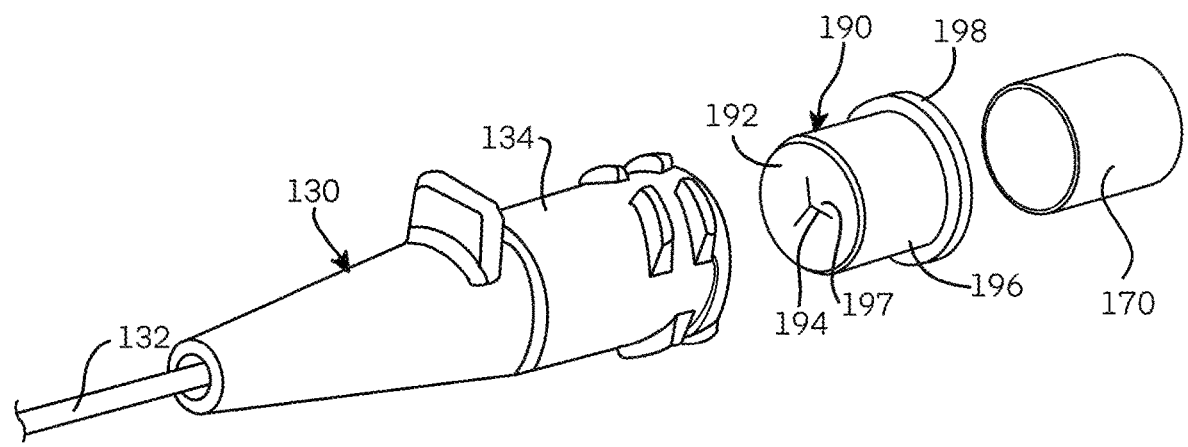
Figure 1E:
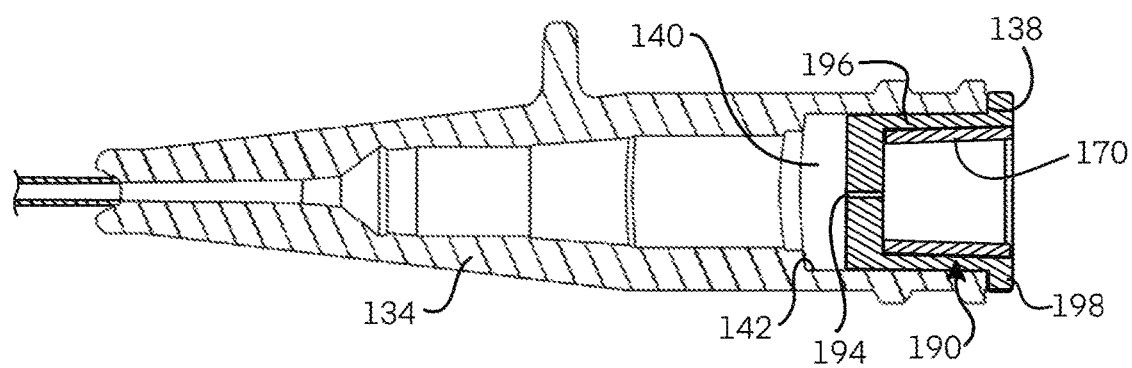

FIGS. 1D and 1E show perspective and cross-sectional views of another variation of a catheter-valve assembly having an insert 170. As shown in FIG. 1D, the insert 170 can be placed within valve 190. The insert 170 can be made of a relatively harder durometer material as compared to the valve 190, which can be made from a softer durometer material. The durometer material can be the same material used for the catheter hub 134 and the male luer 52. The insert 170 has a standard luer taper to receive the male luer 52. As such, male luer 52 slides within and nests against a hard durometer material when attached to the valve 190. For example, in some variations, both the insert 170 and valve 190 can comprise the same durometer material but each component can have different properties via a treatment, coating, additive, etc.

Figure 1F:
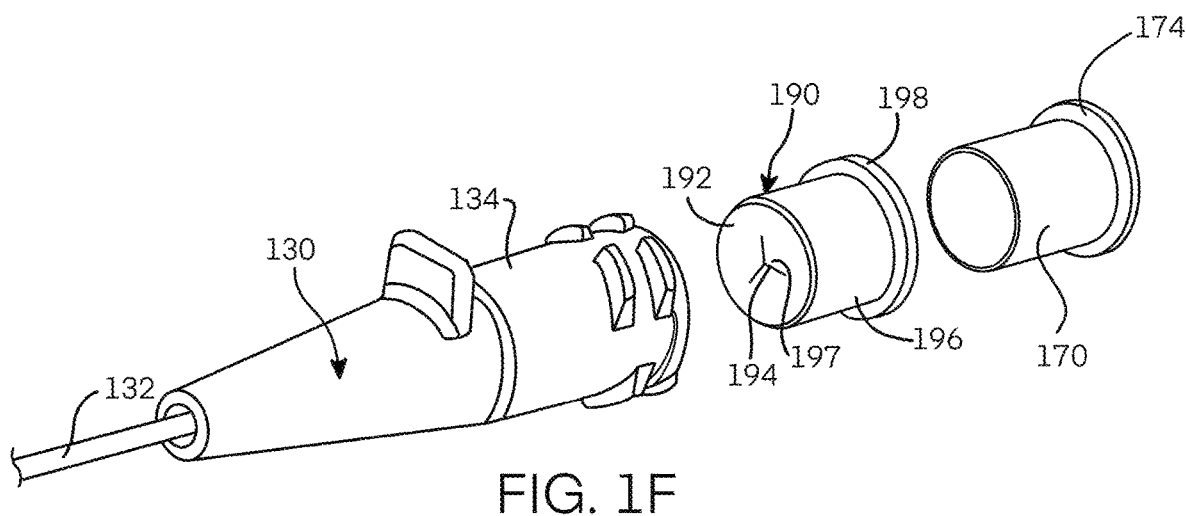
Figure 1G:
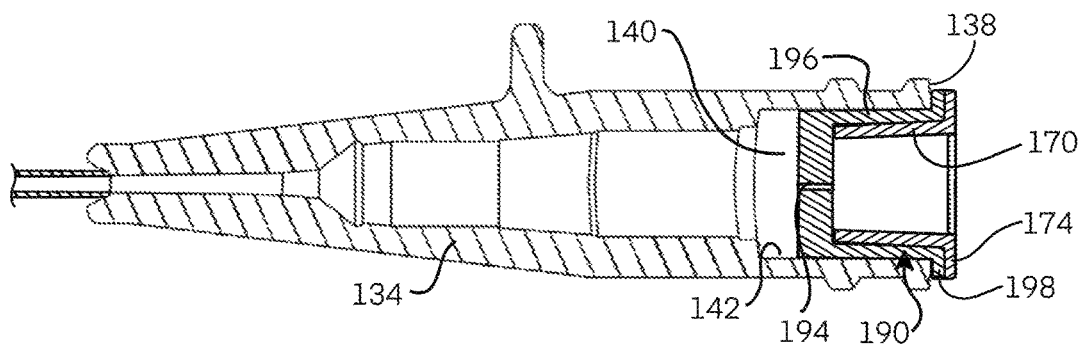
Figure 1H:
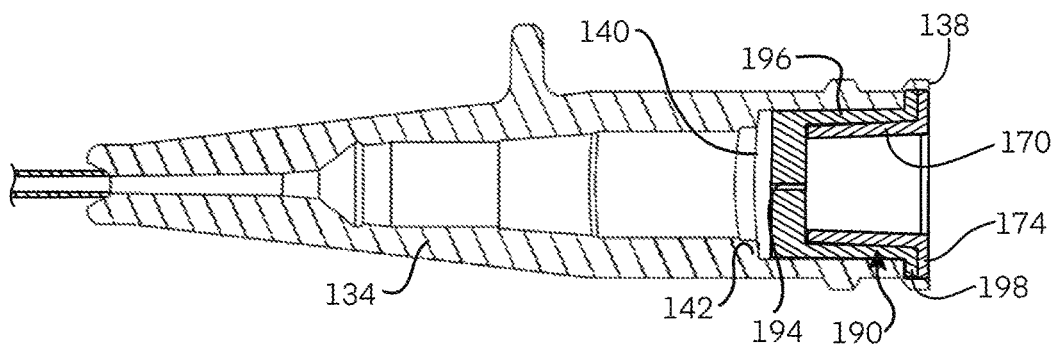

Alternatively, as seen in FIGS. 1F and 1G, the insert 170 can include an insert flange 174 that is positioned against the back surface of the valve 190 or against the back surface 138 of the catheter hub 134. The insert flange 174 can be configured to match or cover the flange portion 198 of valve 190, providing a secure connection to prevent leakage of fluid. It should be understood that the configurations of the catheter-valve assemblies shown in FIGS. 1A to 1C, 2A to 4B, and 6A to 6D can be provided with the insert 170. FIG. 1H illustrates a device similar to that shown in FIG. 1G but where the valve 190 and insert 170 is recessed with a proximal surface 138 of the catheter hub 134. In additional variations, the valve 190 and insert 170 can be recessed within the catheter hub 134.

Figure 1I:
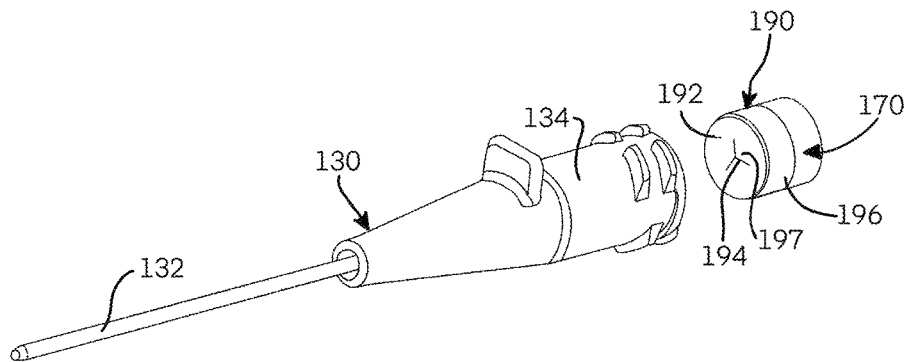
Figure 1J:
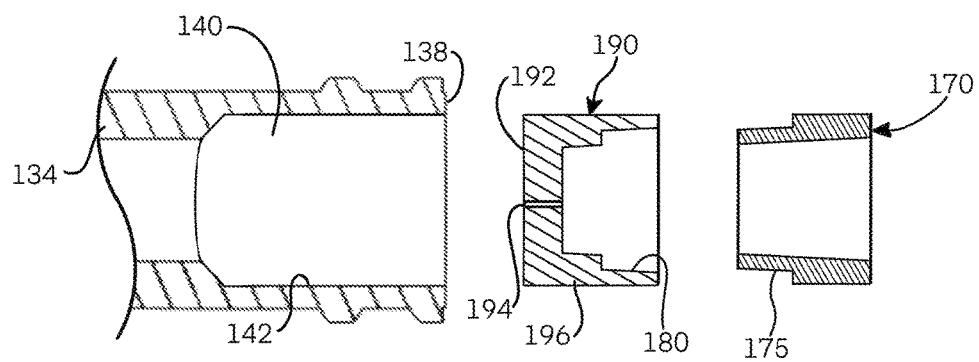
Figure 1K:
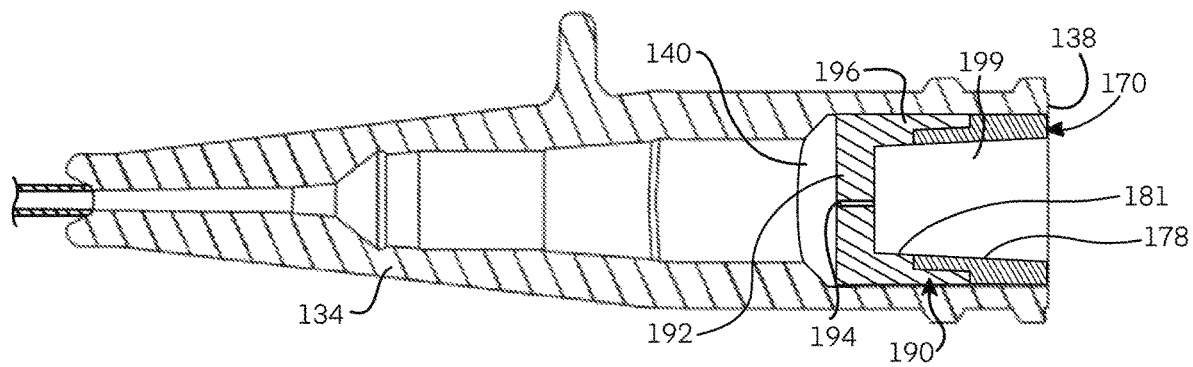

FIGS. 1I to 1K illustrate another variation where a valve 190 is joined to an insert 170 to form a valve assembly having a durometer region selected to sufficiently hard and a distal relatively more elastic region. As noted above, additional variations include an insert 170 have any number of properties that are different from the valve portion (including, but not limited to differences in durometer). FIG. 1J shows a partial cross-sectional exploded view of the catheter hub 134, valve 190 and insert 170 to demonstrate that the insert 170 can include a mating shape 175 that seats with a mating shape 180 in the valve 190. Alternative variations of a valve assembly can include an insert joined with a valve in an end-to-end configuration and without a step or mating surface. FIG. 1K illustrates a cross-sectional view of the assembled insert 170/valve 190 where both components include respective luer tapered surfaces 178 and 181 to provide a continuous luer taper in the joined assembly 170/190. As discussed herein, the valve 190 can include a configuration where the barrier layer/septum 192 is thicker than the largest width of the sidewall 196 that forms the valve cavity 199.

The valve and insert can be joined using adhesives, welding, heat-forming, or any other joining process that allows dissimilar materials to be joined together. Moreover, one or both components can be sealingly joined to a wall of the catheter chamber 140. As noted herein, the insert can comprise a first material and the valve can comprise a second material, wherein the first material and second material comprise different structural properties. In one variation, the materials are formed from different durometer polymers to provide the valve with a greater elasticity relative to the insert. Moreover, variations of the assembly include a luer surface that is smooth or continuous (meaning there are no steps or discontinuities in a surface of the luer forming the valve/insert cavity.

Figure 2A:
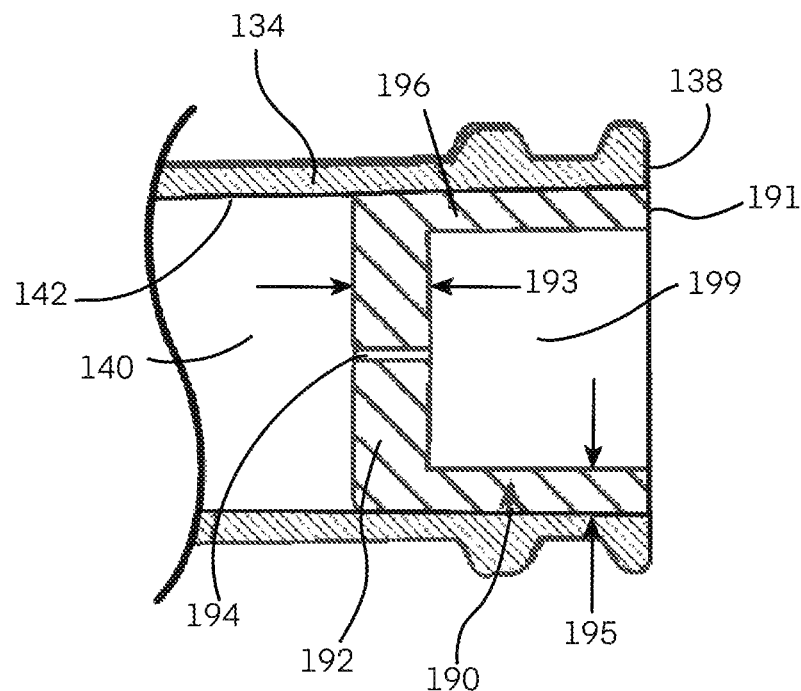
FIGS. 2A and 2B show another cross-sectional view of another variation of a valve.
Figure 2B:
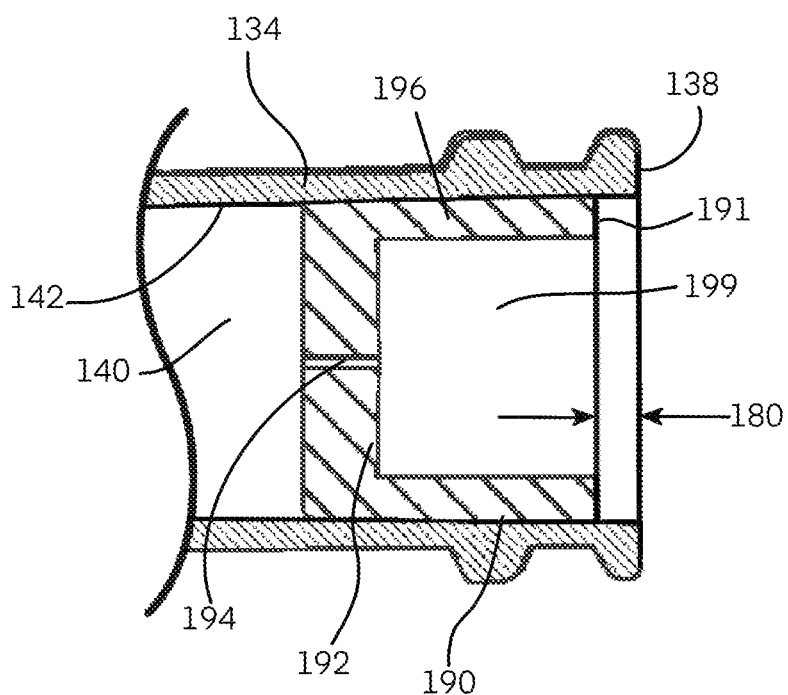

FIGS. 2A and 2B show another cross-sectional view of another variation of a valve 190 for use in a catheter hub 134. As shown, this variation of a valve 190 does not include a flange member at the proximal end 191 of the valve. In this variation, there are no protrusions on an outer wall 196 of the valve 190. In addition, the valve 190 can be positioned within a chamber 140 of the catheter hub 134 such that the proximal end 191 of the valve 190 is flush with a rear face 138 of the catheter hub 134. Alternate variations include the proximal end 191 protruding from the rear face 138 of the hub 134 (not shown). As discussed above, the valve 190 can include a construction where a thickness 195 of the valve wall 196 is less than a thickness 193 of the barrier layer 192 that includes one or more slits 194. FIG. 2B illustrates a variation of a valve 190 similar to that shown in FIG. 2A, where the valve 190 is axially recessed within a chamber of the catheter hub 134 by distance 180.

Figure 3A:
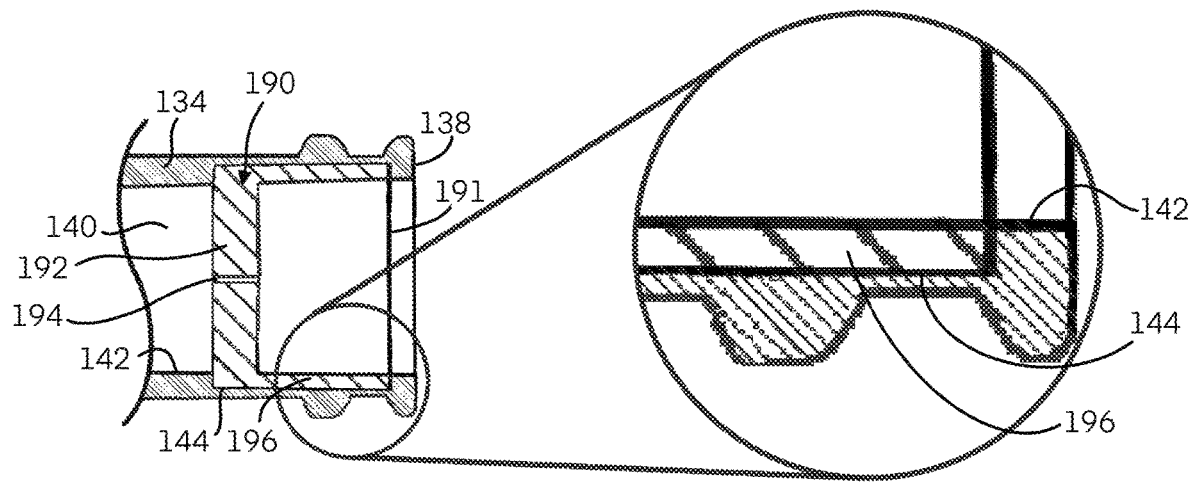
FIGS. 3A and 3B illustrate a cross-sectional view of another variation of a catheter-valve assembly having a valve positioned within a recess within a wall of a chamber of a catheter hub.
Figure 3B:
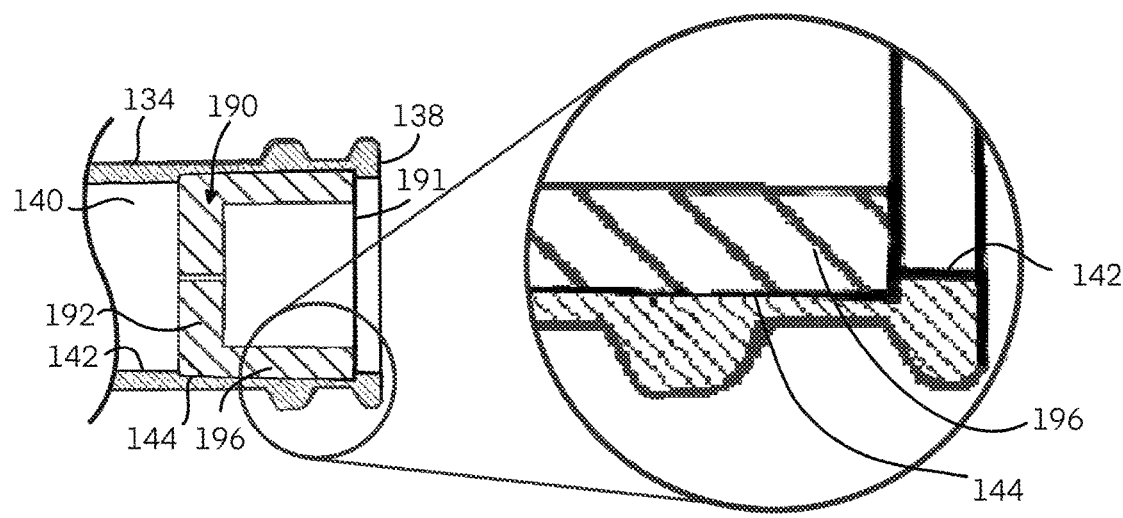

FIGS. 3A and 3B illustrate a cross-sectional view of another variation of a catheter-valve assembly having a valve 190 positioned within a recess 144 within a wall 142 of a chamber 140 of a catheter hub 134. As shown, a valve 190 is positioned within a chamber 140 of a catheter hub 134. While both FIGS. 3A and 3B illustrate a valve 190 where a proximal end 191 of the valve 190 is spaced from a rear end 138 of the hub 134, variations of the assemblies can include any of the valve configurations described herein where the valve is positioned within a recess 144.

FIGS. 3A and 3B illustrate valves 190 where a side wall 196 has a thickness less than a thickness of a barrier wall 192 (as discussed above). However, positioning the valve 190 in a recess 144 located within the wall 142 allows for sizing the internal diameter of the valve cavity 199 closer to an internal diameter of the valve chamber 140 (as discussed below). FIG. 3A illustrates a recess 144 that positions the valve wall 196 to be parallel to the chamber wall 142. Alternatively, FIG. 3B shows a recess 144 that partially extends beyond the valve wall 196.

Figure 4A:
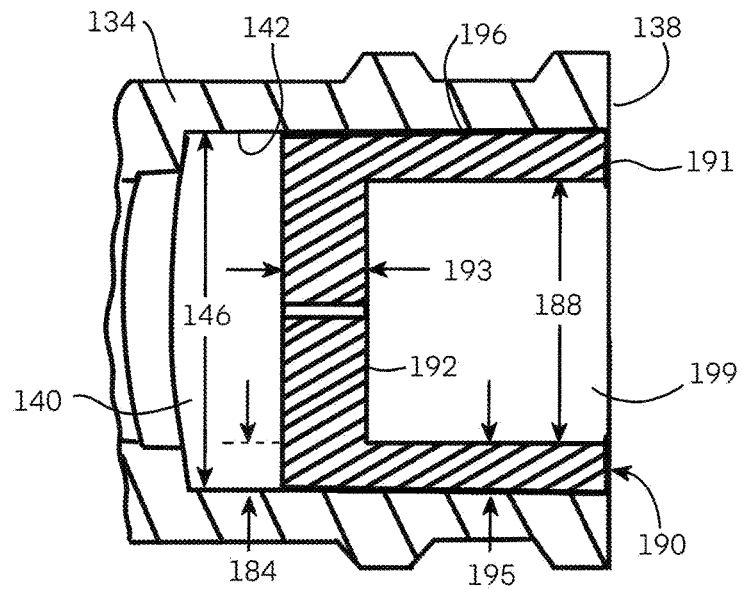
FIGS. 4A and 4B illustrate additional partial cross-sectional views of valves within a chamber of a catheter hub to demonstrate a reduced wall thickness relative to a thickness of a barrier layer.
Figure 4B:
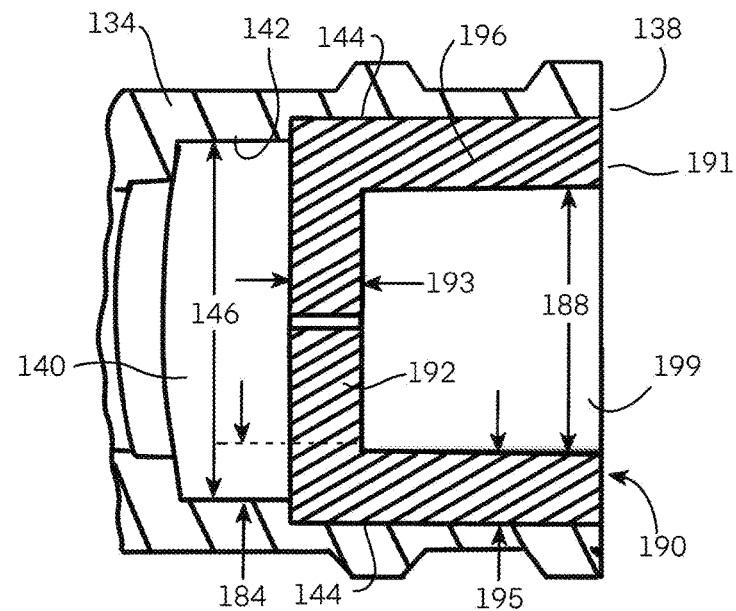

FIGS. 4A and 4B illustrate additional partial cross-sectional views of valves 190 within a chamber 140 of a catheter hub 134 relative to a thickness of a barrier layer. As shown, the chamber 140 of the catheter hub 134 includes an inner diameter 146 adjacent to a barrier layer 192 of the valve 190. FIG. 4A illustrates a configuration where a thickness 193 of the barrier wall 192 (i.e., the wall that opens upon insertion of a luer or other device) is greater than a thickness 195 of the sidewall of the valve 190. This allows for an increased inner diameter 188 of the cavity 199 relative to the inner diameter 146 of the catheter hub 134, which also allows a male luer (not shown) to be sufficiently inserted to open the valve. The increased inner diameter 188 allows for minimizing an offset distance between a surface of the inner diameter 188 of the interior cavity 199 and a surface of the wall 142 of the chamber 140 of the catheter hub 134. The offset distance is generally measured in a radial direction (i.e., perpendicular to the wall). FIG. 4B illustrates an additional variation of a valve 190 where a thickness 195 of the sidewall 196 is close or equal to a thickness 193 of the barrier layer 192. However, the variation shown in FIG. 4B includes a recess 144 within the catheter hub 134. This recess 144 allow for an increased internal diameter 188 of the valve cavity 199 relative to an internal diameter 146 of a chamber 140 of the catheter hub 134 to permit insertion of a male luer.

FIGS. 5A to 5D show a cross-sectional view of a catheter valve assembly 130 to provide an example of a luer fitting 50 being inserted into a valve 190 located within a chamber 140 of the valve assembly 130 to deliver fluids through the catheter tubing 132. The illustrated example shows a valve 190 where a proximal end 191 is flush with a proximal face 138 of the catheter hub 134. However, any of the variations of valves disclosed herein is contemplated to be within the disclosure. As shown, the luer fitting 50 includes threading that engages threading on the catheter hub 134. Variations of assemblies can include fittings without threading. Regardless, the male luer 52 of the luer fitting is inserted into the catheter hub 134 and valve 190.

Figure 5A:
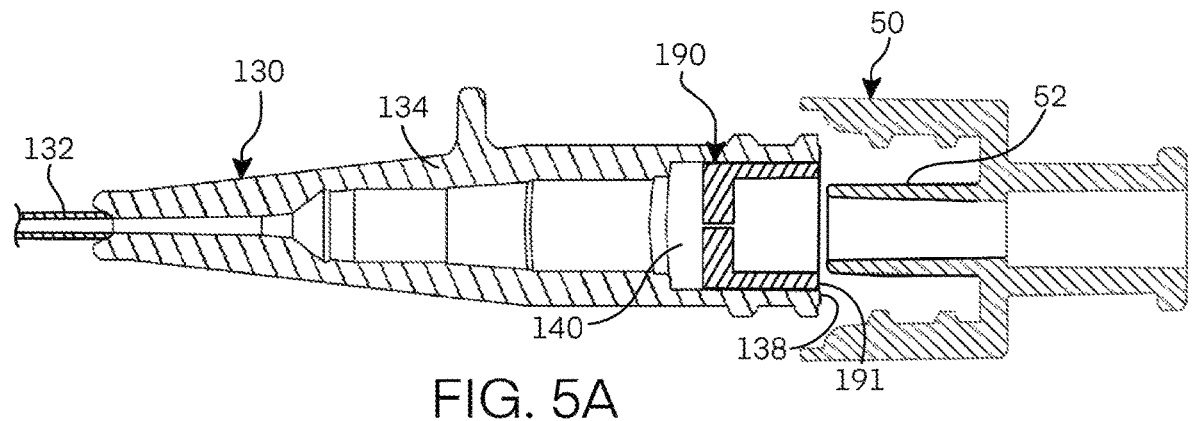
FIGS. 5A to 5G show cross-sectional views of a catheter valve assembly with a luer fitting being inserted into a valve located within a chamber to deliver fluids through the catheter tubing.
Figure 5B:
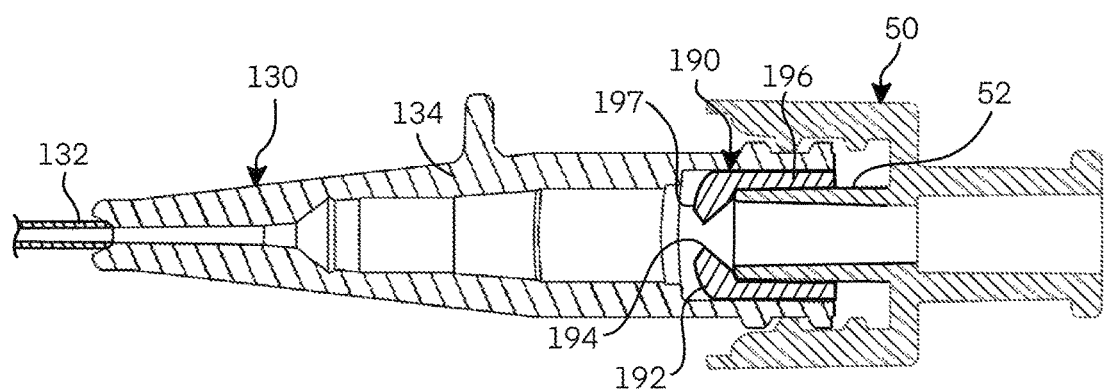

FIG. 5B illustrates insertion of the male luer 52 into the cavity of the valve 190. As shown in FIG. 5B, as a lateral surface of the male luer 52 engages the wall portion 196 of the valve, the wall portion 196 is compressed against a surface of the catheter chamber 140. Further axial advancement of the male luer 52 against a barrier layer 192 causes leaflets 197 formed by the slit 194 in the barrier layer 192 to open in a distal direction, permitting fluid flow through the valve 190. In the variation shown in FIG. 5B, the male luer 52 causes leaflets 197 to deflect to an open position. In some variations, as shown in FIG. 5D, insertion of the male luer 52 into the cavity of the valve 190 causes the distal end of the male luer 52 to a fully open position, while the lateral surface of the male luer 52 engages the wall portion 196 of the valve 190. However, in alternate variations, the leaflets 197 merely deflect to allow sufficient fluid flow.

Figure 5C:
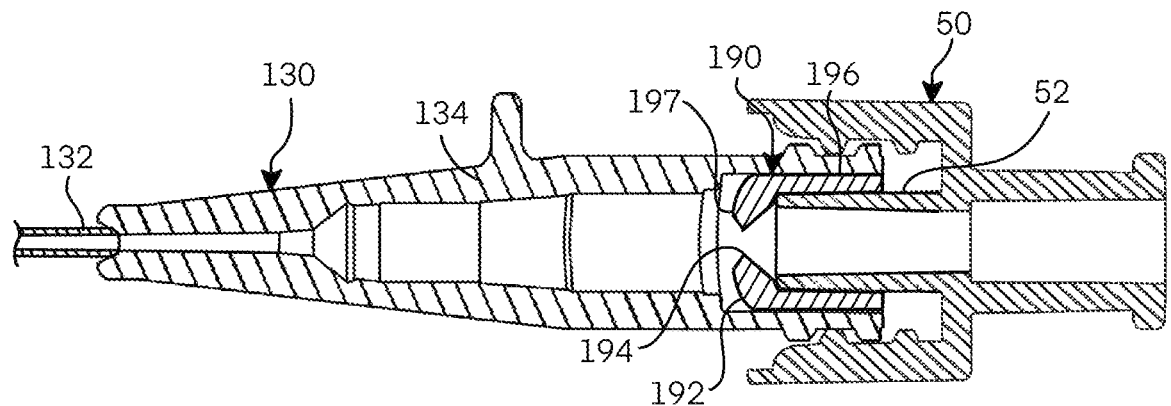
Figure 5D:
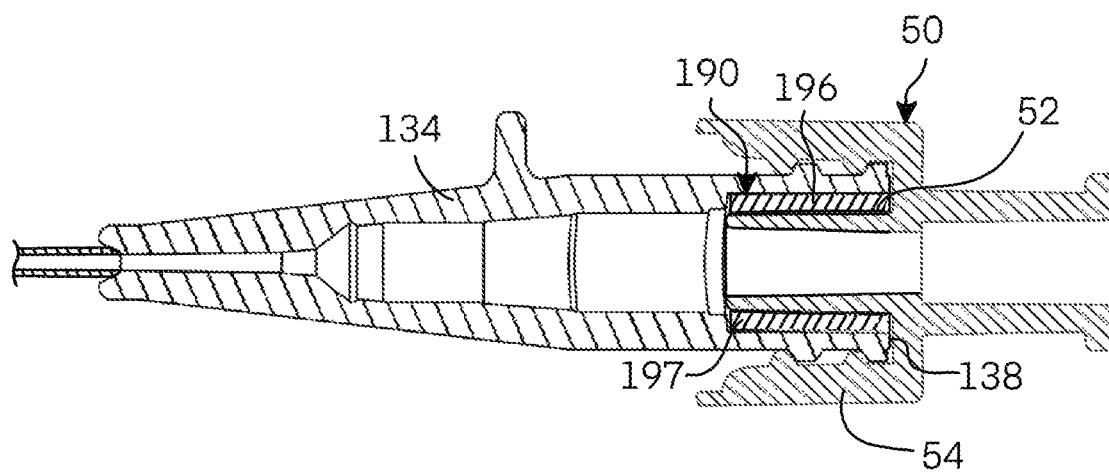

In the variation shown in FIG. 5C, the valve 190 is fabricated from a compliable and resilient material such that insertion of the male luer 52 causes the valve septum 192 to stretch and deform to open the leaflets 197. In such variations, the wall 196 of the valve 190 can be bonded to the interior of the hub. Alternatively, or in addition, a flange 198 (shown in FIG. 1A) can be used to bond or pinch the walls in position so the valve septum 192 stretches instead of moving forward in its normal shape. In those variations where the male luer deforms the valve, the valve operates by elastic deformation rather than fluid pressure. Therefore, the thickness and elasticity of the septum wall 192 permits the valve to return to a closed position when the luer 52 is removed. Moreover, because the valve opens by physical deformation, the closed valve is not subject to leakage caused by the pressure of fluid flowing against the valve.

Ultimately, the connector portion 54 of the luer fitting 50 engages the proximal surface 138 of the catheter hub 134. Removal of the luer fitting 50 from the catheter hub 134 causes the leaflets 197 of the valve formed by the slit to return to a closed configuration.

Figure 5E:
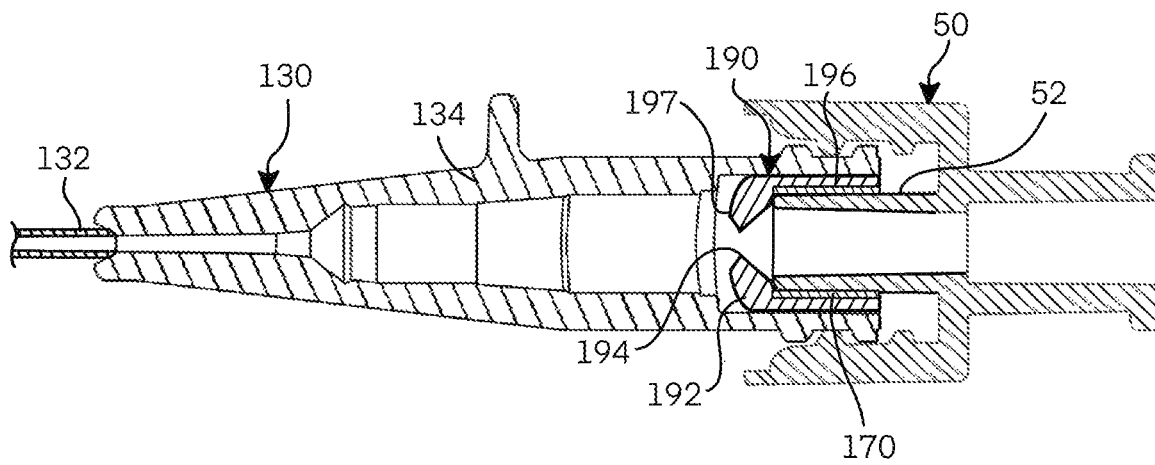

FIG. 5E illustrates another variation of an assembly where a valve includes a material insert. For example, a variation where the wall and flange split between a hard interior top and soft exterior wall and top can be provided to enable the anchoring needed for the stretching of valve 190.

Figure 5F:
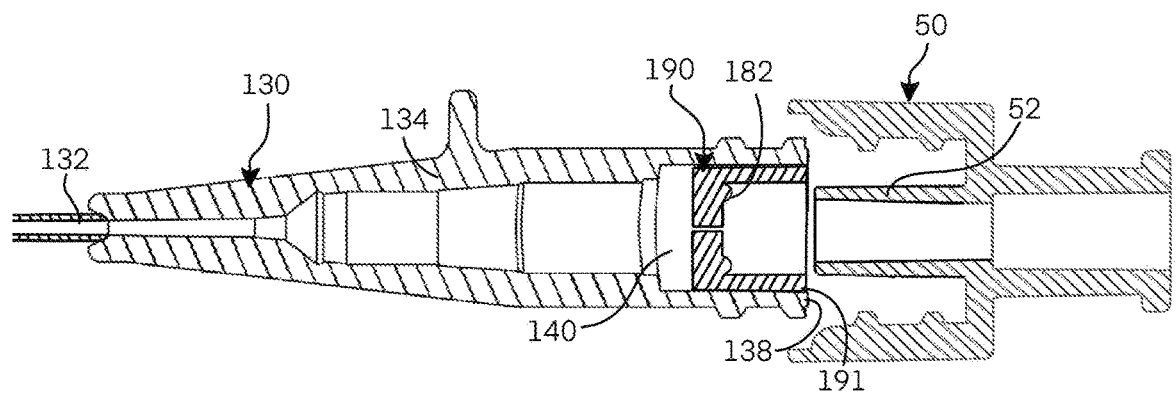
Figure 5G:
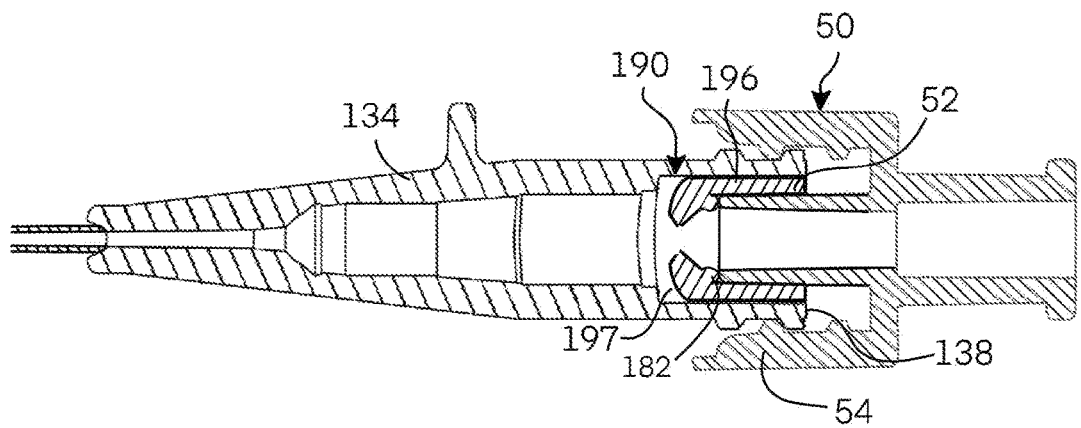

FIGS. 5F to 5G show cross-sectional views of another variation of a catheter-valve assembly having a protrusion 182. The protrusion 182 can be a raised surface, such as a ring on the wall of the septum 192, or one or more protrusions arranged to receive the male luer 52, which in turn assists in opening the valve 190. In variations where the protrusion 182 is a ring on the surface of the septum 192, the ring can be configured with a slit (i.e., contiguous sections) to allow separation when the ring passes across different leaflets 197 of the valve 190. As seen in FIG. 5G, the male luer 52 can be inserted into valve 190 and can push the protrusion 182 distally, stretching the valve 190 and causing the valve to pucker open.

Additionally, the protrusion 182 may be used in combination with the insert 170 described in FIGS. 1D to 1G. In such a configuration, the male luer 52 will stop when wedged into the hard tapered surface of the insert 170. Accordingly, the soft material of the valve can be molded over the harder material of the catheter hub 134 or the insert 170 to help anchor the proximal base of the soft valve. This anchoring can be important when the valve stretches and thins dimensionally due to insertion of the male luer 52. The valve 190 can be stretched about 2 mm or more. The valve leaflets 197 are stretched open and folded to a certain point when the male luer 52 is inserted. After removal of the male luer 52, the valve leaflets 197 return to its original size and sealed position.

Figure 6A:
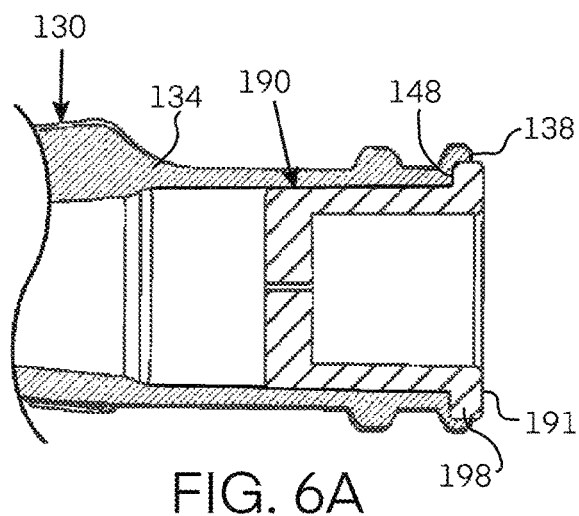
FIGS. 6A to 6D illustrate partial cross-sectional views of additional variations of catheter assemblies having valves with various flange configurations.
Figure 6B:
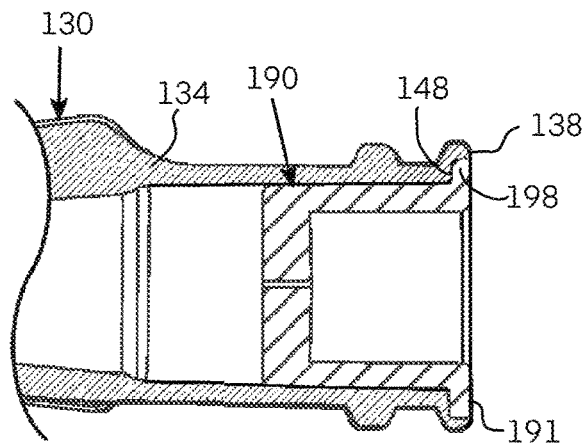
Figure 6C:
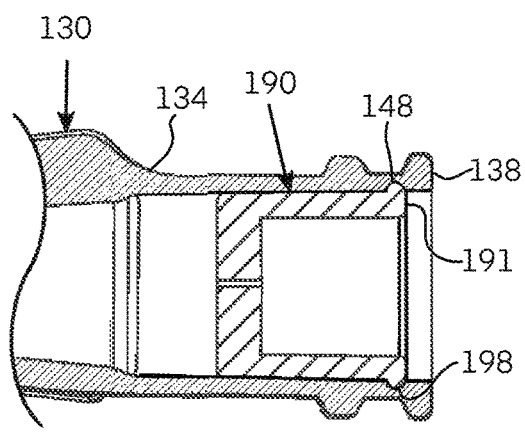
Figure 6D:
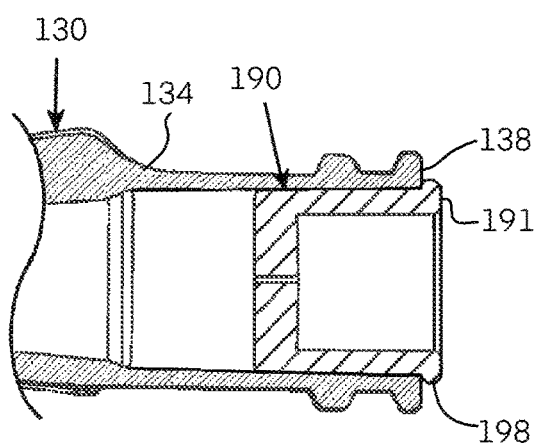

FIGS. 6A to 6D illustrate partial cross-sectional views of additional variations of catheter assemblies 130 having valves 190 with various flange 198 configurations. FIG. 6A illustrates a flange 198 positioned within a recess 148 located in the rear face 138 of the catheter hub 134. As shown, the proximal end 191 of the valve 190 extends beyond the rear face 138 of the catheter hub 134. FIG. 6B illustrates another variation, where the flange 198 is positioned within a recess 148 located in the rear face 138 of the hub 134 but the proximal end 191 of the valve 190 is flush with the rear face 138 of the hub 134. FIGS. 6C and 6D illustrate a flange 198 that comprises a outer edge on an exterior surface of the valve 190. In FIG. 6C the flange 198 is positioned within a recess 148 that is located within the catheter hub 134 such that the proximal end 191 of the valve 190 is also recessed from the back face 138 of the hub 134. FIG. 6D illustrates a similar flange 198 where the proximal end 191 of the valve 190 extends beyond the rear face 138 of the hub 134 but the flange 191 does not entirely cover the rear face 138.

Figure 7A:
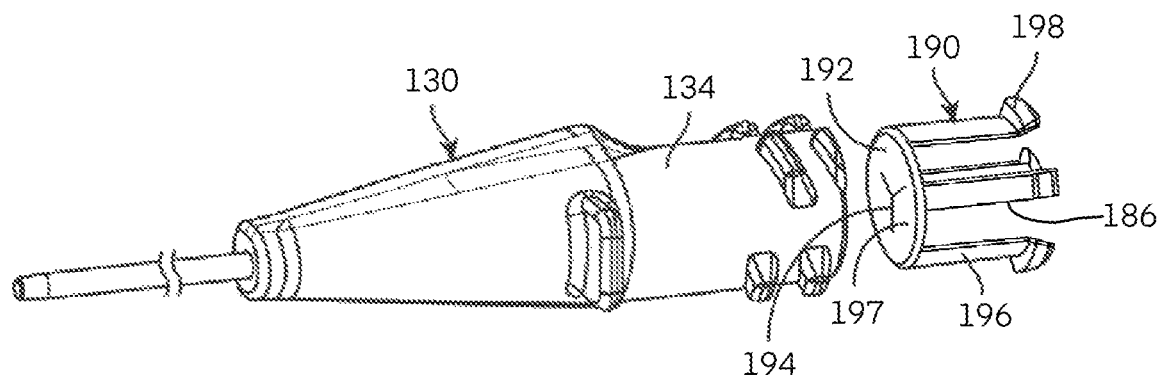
FIGS. 7A to 7D illustrate additional examples of improved valves for use with catheter assemblies as described herein.
Figure 7B:
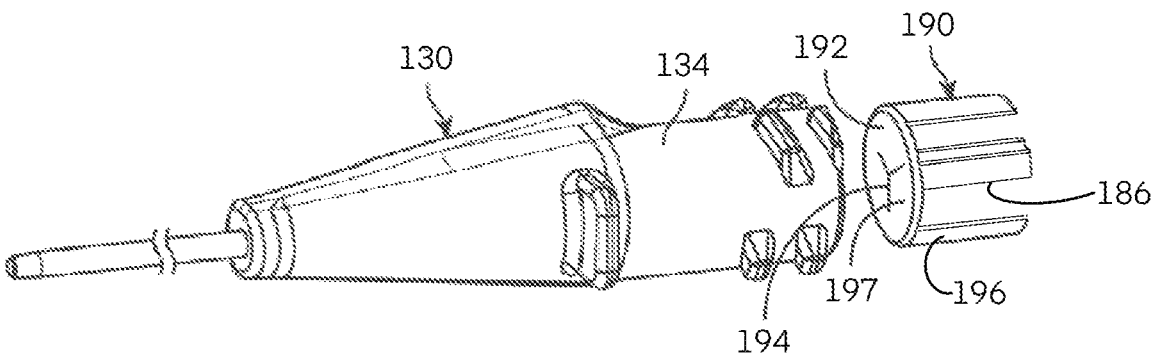
Figure 7C:
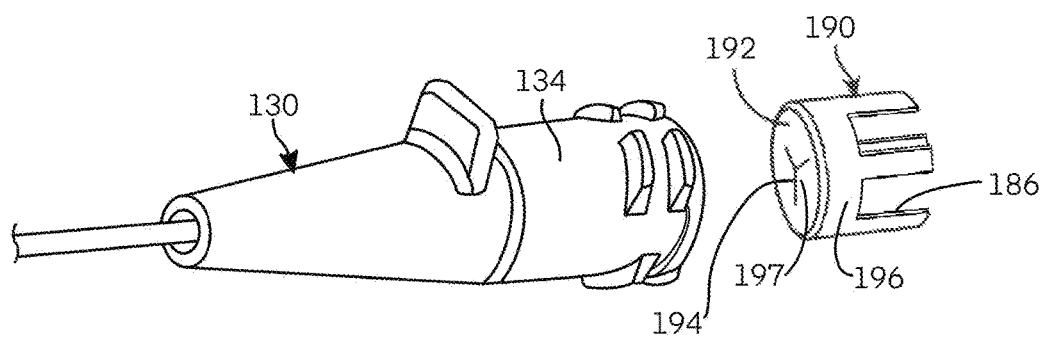
Figure 7D:
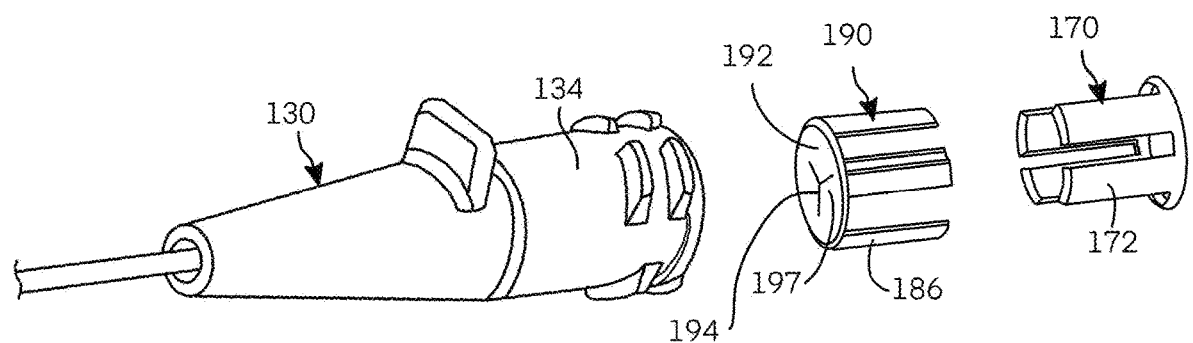

FIGS. 7A to 7D illustrate additional examples of improved valves for use with catheter assemblies 130 as described herein. As shown in FIG. 7A, the valve 190 is seated in the hub 134 of the catheter 130 and includes a barrier layer (or septum) 192 at a distal end that contains one or more slits 194 that define leaflets 197. The valve includes a wall 196 that extends proximally from the barrier layer 192. In this variation, the wall 196 is divided into a number of legs 186 that extend to a segmented flange 198. While the illustrated variation shows 4 legs 186, alternate variations of the valve 190 can include any number of legs (e.g., 1 or more) where the legs do not circumferentially extend over the valve but leave gaps. FIG. 7B illustrates a similar variation of a valve 190 with legs 186 that terminate without a flange. FIG. 7C illustrates an example of a valve 190 where a wall 196 extends circumferentially about the valve but only partially along an axial length where legs 186 extend along a remaining distance of the valve 190. The flange 198, legs 186 and/or wall 196 of the valves shown in FIG. 7A to 7C can be positioned within a recess in the chamber of the catheter hub (e.g., see 144 or 148 above) to partially or fully align the interior diameter of the valve with a wall of the catheter chamber. Regarding the variations of the catheter-valve assembly shown in 7D, an insert 170 can have legs 172 as shown in FIG. 7D. To form a barrier between the insert 170 and the catheter hub 134, the insert 170 can fill in the gaps between legs 186. When the insert 170 is placed within valve 190, the legs 186 can be sealed to prevent leakage of any fluid therethrough. In additional variations, an insert 170 can have any number of properties that are different from the valve 190. The legs 172 of the insert 170 will minimize any gap that may form with the legs of the valve 190 when inserted.

The previous description of the disclosed embodiments is provided to enable any person skilled in the art to make or use the present invention. Various modifications to these embodiments will be readily apparent to those skilled in the art, and the generic principles defined herein can be applied to other embodiments without departing from the spirit or scope of the invention. For example, a wide variety of materials may be chosen for the various components of the embodiments. It is therefore desired that the present embodiments be considered in all respects as illustrative and not restrictive, reference being made to the appended claims as well as the foregoing descriptions to indicate the scope of the invention.

The invention claimed is:

1. A valve assembly configured for use with a male luer having a distal end, a lateral surface and a connector portion, the valve assembly comprising:
    a hub configured to receive the male luer in a proximal end;
    a valve coupled to a chamber within the hub and comprising a barrier layer at a far end and a wall portion; the wall portion extending proximally from the barrier layer towards a near end of the valve, the wall portion defining a valve cavity therein, the barrier layer having at least one slit extending therethrough;
    wherein an offset distance, measured between a surface of the wall portion in the valve cavity and a surface of the chamber adjacent to the barrier layer at the far end of the valve, is less than a thickness of the barrier layer;
    where the valve is configured for positioning in the hub such that the wall portion engages the surface of the chamber within the hub; and
    wherein the barrier layer is configured to deform by elastic deformation rather than fluid pressure such that insertion of the male luer into the valve cavity causes the distal end of the male luer to deform the barrier layer and open the at least one slit to permit fluid flow through the barrier layer, while the lateral surface of the male luer engages the wall portion at an interior of the valve cavity causing the wall portion to engage the surface of the chamber.

2. The valve assembly of claim 1, wherein the at least one slit forms a plurality of leaflets in the barrier layer.

3. The valve assembly of claim 2, wherein a perimeter of the at least one slit is limited to the barrier layer such that the plurality of leaflets do not extend into the wall portion.

4. The valve assembly of claim 2, wherein the at least one slit is branched such that the plurality of leaflets comprises at least three leaflets.

5. The valve assembly of claim 2, wherein a thickness of each of the plurality of leaflets is the same.

6. The valve assembly of claim 1, wherein an entire outer surface of the wall portion contacts the surface of the chamber.

7. The valve assembly of claim 1, wherein an entire outer surface of the wall portion comprises a cylindrical shape having a uniform outer diameter.

8. The valve assembly of claim 1, further comprising a flange portion at the near end of the valve.

9. The valve assembly of claim 8, wherein the flange portion comprises a raised surface on an exterior surface of the valve.

10. The valve assembly of claim 8, wherein a proximal end of the flange portion extends beyond the proximal end of the hub.

11. The valve assembly of claim 10, wherein the flange portion partially covers the proximal end of the hub.

12. The valve assembly of claim 1, wherein the valve is axially recessed within the hub.

13. The valve assembly of claim 1, wherein the wall portion includes at least one or more gaps to form at least one or more legs.

14. The valve assembly of claim 13, where the at least one or more legs extend partially along an axial length of the valve.

15. The valve assembly of claim 1, wherein the near end of the valve is flush with the proximal end of the hub.

16. The valve assembly of claim 1, further comprising an insert positioned within the valve, wherein the insert is configured to receive the male luer.

17. The valve assembly of claim 1, further comprising a raised surface positioned within the valve, wherein upon insertion of the male luer, the raised surface is configured to be pushed by the male luer to open the valve.

18. The valve assembly of claim 1, further comprising an insert coupled to the valve, wherein the insert comprises a first material and the valve comprises a second material, wherein the first material and second material comprise different structural properties.

19. The valve assembly of claim 18, wherein the first material comprises a first durometer and the second material comprises a second durometer being less than the first durometer such that the second material comprises a greater elasticity relative to the first material.

20. The valve assembly of claim 18, the insert comprises a first mating surface coupled to a second mating surface of the valve, a first portion of the valve cavity adjacent to an insert cavity formed by the insert, wherein a luer surface of the valve cavity smoothly transitions from a luer surface of the insert cavity.

21. A valve assembly configured for use with a male luer having a distal end, a lateral surface and a connector portion, the valve assembly comprising:
   a hub configured to receive the male luer in a proximal end:
   a valve coupled to a chamber within the hub and comprising a barrier layer at a far end and a wall portion;
   the wall portion extending proximally from the barrier layer towards a near end of the valve, the wall portion defining a valve cavity therein, the barrier layer having at least one slit extending therethrough, wherein an entire outer surface of the wall portion contacts an inner surface of the chamber;
   wherein an offset distance, measured between an inner surface of the wall portion in the valve cavity and the inner surface of the chamber adjacent to the barrier layer at the far end of the valve is less than a thickness of the barrier layer;
   where the valve is configured for positioning in the hub such that the wall portion engages the inner surface of the chamber within the hub; and
   wherein insertion of the male luer into the valve cavity causes the distal end of the male luer to open the at least one slit to permit fluid flow through the barrier layer, while the lateral surface of the male luer engages the wall portion at an interior of the valve cavity causing the wall portion to engage the inner surface of the chamber.

22. The valve assembly of claim 21, wherein the valve is axially recessed within the hub.

23. The valve assembly of claim 21, wherein a proximal end of the valve is flush with the proximal end of the hub.

24. A valve assembly configured for use with a male luer having a distal end, a lateral surface and a connector portion, the valve assembly comprising:
   a hub configured to receive the male luer in a proximal end:
   a valve coupled to a chamber within the hub and comprising a barrier layer at a far end and a wall portion, wherein an entire outer surface of the wall portion comprises a cylindrical shape having a uniform outer diameter;
   the wall portion extending proximally from the barrier layer towards a near end of the valve, the wall portion defining a valve cavity therein, the barrier layer having at least one slit extending therethrough;
   wherein an offset distance, measured between an inner surface of the wall portion in the valve cavity and a surface of the chamber adjacent to the barrier layer at the far end of the valve is less than a thickness of the barrier layer;
   where the valve is configured for positioning in the hub such that the wall portion engages the surface of the chamber within the hub; and
   wherein insertion of the male luer into the valve cavity causes the distal end of the male luer to open the at least one slit to permit fluid flow through the barrier layer, while the lateral surface of the male luer engages the wall portion at an interior of the valve cavity causing the wall portion to engage the surface of the chamber.

25. The valve assembly of claim 24, wherein the valve is axially recessed within the hub.

26. The valve assembly of claim 24, wherein a proximal end of the valve is flush with the proximal end of the hub.

\* \* \* \* \*